(12) United States Patent
Kuusela

(10) Patent No.: US 7,460,233 B2
(45) Date of Patent: *Dec. 2, 2008

(54) PASS-LINE AND TILT INSENSITIVE SENSOR

(75) Inventor: Reijo Kuusela, Kuopio (FI)

(73) Assignee: Honeywell International Inc., Morristown, NJ (US)

( * ) Notice: Subject to any disclaimer, the term of this patent is extended or adjusted under 35 U.S.C. 154(b) by 110 days.

This patent is subject to a terminal disclaimer.

(21) Appl. No.: 11/269,118

(22) Filed: Nov. 8, 2005

(65) Prior Publication Data

US 2007/0103674 A1    May 10, 2007

(51) Int. Cl.
G01N 21/84 (2006.01)
G01N 21/55 (2006.01)

(52) U.S. Cl. .......... 356/430; 356/431; 356/445

(58) Field of Classification Search .......... 356/429–431
See application file for complete search history.

(56) References Cited

U.S. PATENT DOCUMENTS

| | | | | |
|---|---|---|---|---|
| 3,636,361 A | * | 1/1972 | Bowers | 250/349 |
| 4,019,066 A | * | 4/1977 | Lucas et al. | 250/559.16 |
| 4,644,174 A | * | 2/1987 | Ouellette et al. | 250/559.01 |
| 4,812,665 A | | 3/1989 | Puumalainen et al. | |
| 4,830,504 A | | 5/1989 | Frohardt et al. | |
| 4,945,253 A | | 7/1990 | Frohardt | |
| 5,229,835 A | * | 7/1993 | Reinsch | 356/600 |
| 5,943,133 A | | 8/1999 | Zeylikovich et al. | |
| 5,991,046 A | * | 11/1999 | Shakespeare et al. | 356/429 |
| 6,031,620 A | | 2/2000 | Typpo | |
| 6,233,053 B1 | | 5/2001 | Preston et al. | |
| 6,404,502 B2 | | 6/2002 | Preston et al. | |
| 6,687,015 B1 | | 2/2004 | Waller et al. | |
| 6,762,839 B2 | | 7/2004 | Zeylikovich et al. | |
| 6,858,436 B2 | | 2/2005 | Zenhausern et al. | |
| 2004/0005157 A1 | * | 1/2004 | Akita | 399/45 |
| 2006/0243931 A1 | * | 11/2006 | Haran et al. | 250/574 |

FOREIGN PATENT DOCUMENTS

WO    WO 98/49541    11/1998
WO    WO 01/20308    3/2001

OTHER PUBLICATIONS

Specular Gloss of Paper and Paperboard at 75 Degrees, Tappi Standard, T480- om-90, 1990, p. 1-7, XP002912676.

* cited by examiner

*Primary Examiner*—Tarifur Chowdhury
*Assistant Examiner*—Tara S Pajoohi
(74) *Attorney, Agent, or Firm*—Munck Carter, P.C.

(57) ABSTRACT

The devices, systems and methods may continuously detect surface characteristics of a sample surface at a tilt. The exemplary system may have a conveying device for moving a sample surface, a light source for reflecting a beam of light off the sample surface, and a light detector with a light detection surface for continuous light detection. A lens may be used to reflect the beam of light from the sample surface and focus the beam of light on the light detection surface of the light detector. The area of the beam of light at the point of focus on the light detection surface may be unequal to the light detection surface. A reference analyzer may be used to determine the optical surface based on a comparison of the reflected light received with known reflected light values for known sample surfaces.

20 Claims, 5 Drawing Sheets

PASS-LINE AND TILT INSENSITIVE SENSOR

FIELD OF THE INVENTION

The present invention relates generally to detecting surface characteristics of a sample surface, and more particularly to continuous detecting of surface characteristics of a moving sample surface.

BACKGROUND OF THE INVENTION

During the paper making process water, refined pulp and other additives are combined to give the finished paper the desired properties. The mix is spread over a mesh screen which forms the paper and lets the water be extracted. The paper then travels through different processes and machines designed to remove the water from the paper. After the paper is dry, the paper is run between drums to give the desired smoothness. This process may be referred to as calendering the paper. The more times paper is calendered the less bulk it has but the smoother the finish of the paper. To create glossy paper, uncoated paper may be coated with a paint-like product and buffed by rollers under very high pressure, to create a shiny appearance. This process may be referred to as super-calendering. Additional varnish layers may be applied to paper during the printing process to provide a gloss surface on the paper. The gloss surface may also protect the paper from the surrounding environment. During the various manufacturing process a continuous roll of paper weaves throughout the machinery of the press. Rolls and presses are used to move the paper between the various manufacturing processes.

Figure 1A:
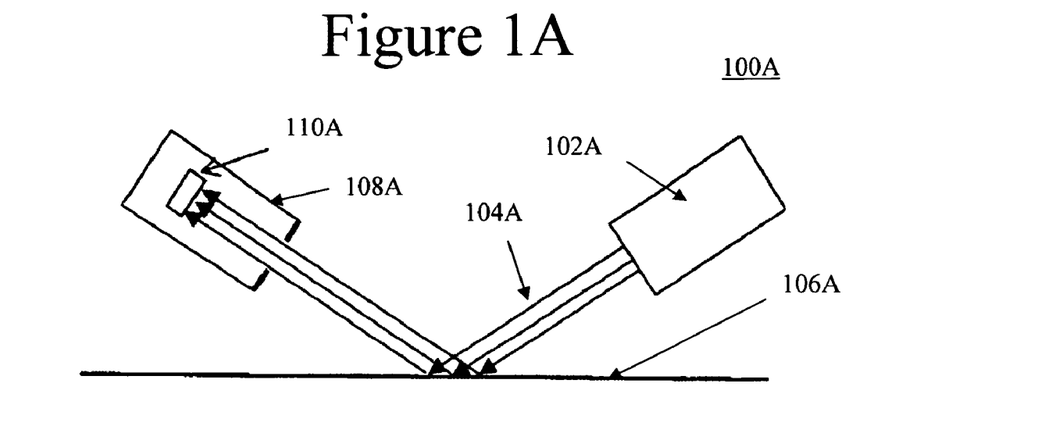
FIG. 1A is a generalized schematic of a prior art gloss sensor.

To ensure that the paper surface has received the correct amount of gloss, sensors are used to measure the gloss of sample surfaces. Referring to FIG. 1A, sensor 100A may have a light source 102A for providing a light beam 104A to illuminate sample surface 106A at a pass-line. Light beam 104A is reflected off sample surface 106A. The intensity of the reflected light is measured with light detector 108A. The reflected light is measured by light detecting surface 110A of light detector 108A to determine the light intensity of the reflected light. The gloss level is calculated by determining the ratio of the reflecting light beam intensity to the intensity of the illuminating light beam. The intensities of the reflected light are compared with known values of intensity for various gloss sample surfaces.

Figure 1B:
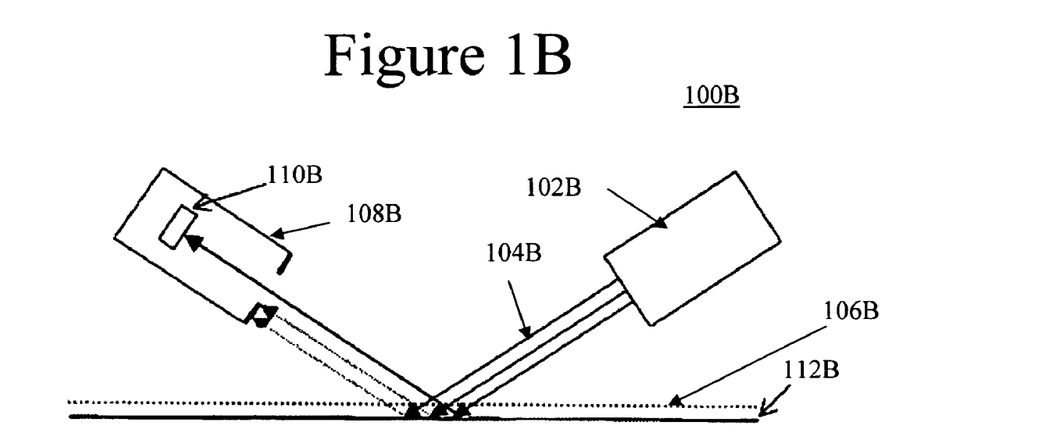
FIG. 1B is a generalized schematic of a prior art gloss sensor with flutters and waves of the sample surface at the pass-line.

Referring to FIG. 1B, as the paper moves along the manufacturing process, sample surface 106B of a web of paper may flutter or wave due to vibrations imparted by the devices, applicators, and other machinery used in the manufacturing process. The flutter or wave may cause the sample surface 106B to move to a new sample surface location 112B. The movement of the sample surface 106B may cause errors to the measured gloss values because the optical arrangement of the gloss sensor system may require a very precise geometry in order to operate in a correct manner.

Figure 1C:
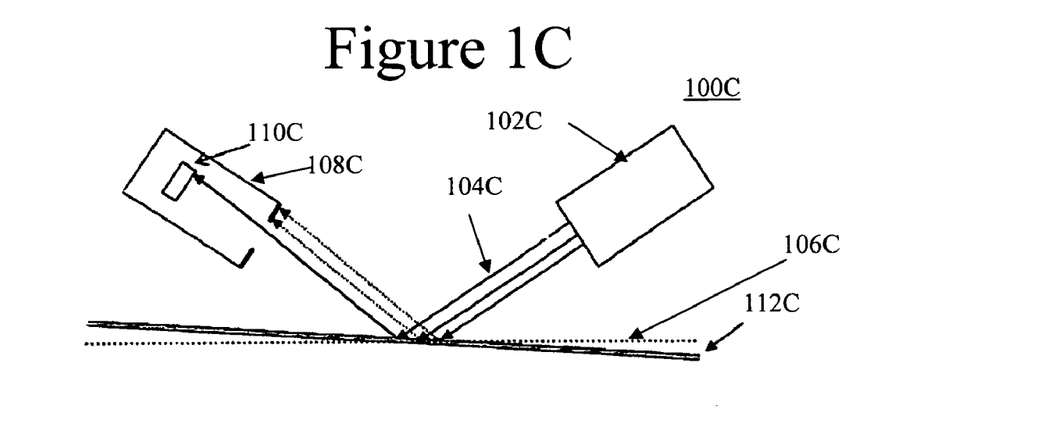
FIG. 1C is a generalized schematic of a prior art gloss sensor with tilt of the sample surface at the pass-line.

Referring to FIG. 1C, as the paper moves along the manufacturing process, the sample surface 106C of the web of paper may tilt and/or cup due to shifts in the web of paper in both lateral and longitudinal directions. The tilt may cause the sample surface 106C to shift to a new sample surface angle 112C. This may be problematic with on-line measurement applications. The tilt of the sample surface 106C may cause errors to the measured gloss values. The erratic sensor response is caused by the optical arrangement of the gloss measurement. The optics may require a very precise geometry. The light source 102C may reflect the light beam 104C off the sample surface 106C exactly onto the light detecting surface 108C of the light detector 110C.

If sample surface 106B, 106C moves or tilts, some part of the reflected light rays may be lost and the measured signal will be erratic. The current state of the art may provide for precise measurements in a laboratory setting when the sample position can be easily controlled but, as explained above, such control is not easily obtained in a manufacturing environment.

In paper and board manufacturing, non-touching measurement principles may be preferred over sensor techniques that make contact with the paper web. In addition, paper web stabilization techniques such as mechanical sheet stabilizers are also not preferred. For example, the use of mechanical sheet stabilizers can cause scoring on the product surface. Due to such markings, it may be impossible to use sheet stabilizers in certain applications. Also, sheet stabilizers may tend to increase dust and dirt problems by rubbing the moving web. The cross-direction profiles of paper and board webs can have many types of deviations from a straight line. For example, the base cross profile can be warped in many different directions. Because warping or scoring of paper the optimal position of the paper web for on-line gloss measurement is very difficult and sometimes impossible to guarantee.

Accordingly, an efficient and effective device, method, and system is needed for detecting surface characteristics of a sample surface. In addition, the system and method may provide for detecting surface characteristics of a moving sample surface.

SUMMARY OF THE INVENTION

It is, therefore, an object of the present invention to provide devices, systems, and methods for detecting surface characteristics of a sample surface at a tilt where the surface is stable or moving. According to an exemplary embodiment of the present invention, the device may have a conveying device for moving a sample surface. The device may also have a light source for reflecting a beam of light off the sample surface and a light detector with a light detection surface for continuous light detection. A lens may be used for receiving the beam of light reflected from the sample surface and focusing the beam of light on the light detection surface of the light detector. The area of the beam of light prior to the lens may be unequal to an area of a lens receiving surface. A reference analyzer may determine the optical properties of the analyzed surface based on a comparison of the reflected light received with known reflected light values for known sample surfaces.

In an alternate embodiment, the area of the focused beam of light may be larger than the area of the light detection surface and the reference analyzer comparison may be based on the area of the detection surface. In another embodiment, the area of the focused beam of light may be smaller than the area of the light detection surface and the reference analyzer comparison may be based on the area of the focused beam of light prior to the lens. In another embodiment, the reference analyzer may determine the gloss, the deviation of gloss, the sparkle spot size, or the number of spot sizes. In another embodiment, the light detector may be a Charge Coupled Device (CCD) camera., Charge Coupled Device (CCD) array, Complementary Metal Oxide Semiconductor (CMOS) camera, Complementary Metal Oxide Semiconductor (CMOS) array, photodiode array or photodiode. In yet another embodiment, the sample surface may be the surface of a moving web of paper. In yet another embodiment, the reference analyzer may compare the intensity of reflected light received with known intensity reflected light values of known sample surfaces.

According to an exemplary embodiment of the present invention, the method may involve the following steps. The sample surface may be conveyed along a mechanized process at a tilt. A beam of light is emitted onto the sample surface and reflected off the sample surface. The beam of light reflected from the sample surface is focused onto a light detection surface of a light detector. The area of the beam of light prior to the lens is unequal to an area of a lens receiving surface. The beam of light is focused by the lens onto the light detection surface of the light detector continuously. The optical surface is determined based on a comparison of the reflected beam of light received with known reflected light values for known sample surfaces.

BRIEF DESCRIPTION OF THE DRAWINGS

The above and other objectives and advantages of the present invention will be apparent upon consideration of the following detailed description, taken in conjunction with the accompanying drawings, in which like reference numbers refer to like parts throughout, and in which.

DETAILED DESCRIPTION OF THE INVENTION

A sensor is used to measure the gloss of a sample surface by directing a beam of light at the sample surface and electronically comparing the reflectance of the sample surface to that of a standardization surface having a known gloss. According to an exemplary light source embodiment of the present invention, the light beam illuminating the sample surface may have a larger area than the light beam accepted and detected by the light detector. The illuminated area of the sample surface is larger than the area, which is seen by the light detector. The illuminated area of the sample surface is larger than the measurement area, which is seen by the light detector. This arrangement allows the sample surface to change its position within predefined geometrical limits. The measurement area of the light detector remains in the illuminated area as the sample surface moves. The intensity of reflected light received by the light detector is compared with known values of intensity for various gloss sample surfaces based on the area of the light detector.

According to an exemplary light detector embodiment, a narrow light beam is used to illuminate the sample surface and is reflected onto a light detector. The illuminated area of the sample surface is smaller than the area which is seen by the light detector. The illuminated area of the sample surface is smaller than the measurement area, which is seen by the light detector. This arrangement allows the sample surface to change its position within the geometrical limits. The measurement area of the beam remains within the detection area of the light detector as the sample surface moves. The intensity of reflected light received by the light detector is compared with known values of intensity for various gloss sample surfaces based on the area of the beam of light. The various embodiments described herein may comply with various known standards, for example, the Technical Association of the Pulp and Paper Industry (TAPPI) standards as well as other known industry and government standards.

According to an exemplary lens embodiment, a light beam may illuminate the sample surface and is reflected onto a light detector. The illuminated area of the sample surface may be collimated to a beam smaller than the area which is seen by the light detector. The illuminated area of the sample surface may be collimated to a beam larger than the area which is seen by the light detector. This arrangement allows the sample surface to change its position within the geometrical limits in a similar fashion as previously described in the light detector and light source embodiment. The measurement area of the beam remains within the detection area of the light detector as the sample surface moves. The intensity of reflected light received by the light detector is compared with known values of intensity for various gloss sample surfaces based on the area of the beam of light or the area of the light detector, respectively.

Figure 2A:
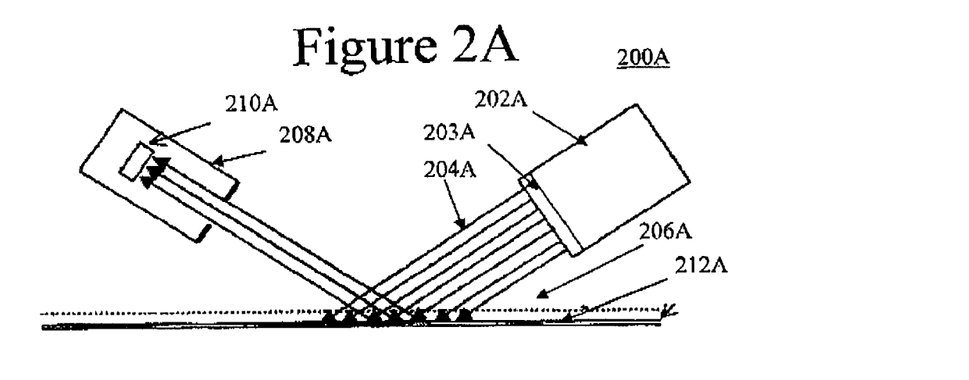
FIG. 2A is a generalized schematic of a sensor used to implement the exemplary light source embodiment of the present invention.

Referring to FIG. 2, sensor 200A may include light source 202A with lens 203A for providing light beam 204A to illuminate sample surface 206A at a pass-line. Light source 202A and lens 203A provide light beam 204A with an area larger than light detection surface 210A of the light detector 208A. Light source 202A provides a focused beam of light or collimated light beam for example a laser or other method of providing a focused beam of light. Light source 202A may be a variety of electromagnetic energy sources. For example, the light source may emit a non-visible wavelength of light energy to prevent interference by overhead lighting or other sources of light within the manufacturing process.

Sample surface 206A may be a variety of materials handled in a manufacturing process or mechanized process. For example, sample surface 206A may be a web of paper or board. The web is continuously moved throughout the manufacturing process using various rollers, presses, and other machinery. Sample surface 206A is not limited to a web of paper. Sample surface 206A may be individual sheets of material that are advanced on a conveyor belt or devices for transporting sheets of material.

Sensor 200A provides accurate measurements of the sample surface without or with a reduced need for stabilization. Light beam 204A is reflected off the sample surface 206A. The intensity of the reflected light is measured with a light detector 208A. The reflected light is measured by light detecting surface 210A of light detector 208A to determine the light intensity of the reflected beam of light 204A. The light detecting surface 210A may define the area seen by the light detector 208A. The measurement geometry and optics may be regulated by industry standards, for example, Technical Association of the Pulp and Paper Industry (TAPPI) T480.

The light detecting surface 210A converts the beam of light 204A into electrical current. The light detecting surface 210A may be composed of a variety of devices, for example, Charge Coupled Device (CCD) camera, Charge Coupled Device (CCD) array, Complementary Metal Oxide Semiconductor (CMOS) camera, digital Complementary Metal Oxide Semiconductor (CMOS) imaging, or photodiodes. The light detector 208A may be a continuous detecting device, for example, a video camera. The signal generated by light detector 208A may be analog or converted to a digital signal for processing. The signal of light detector 208A is fed into a reference analyzer (not shown).

Figure 2B:
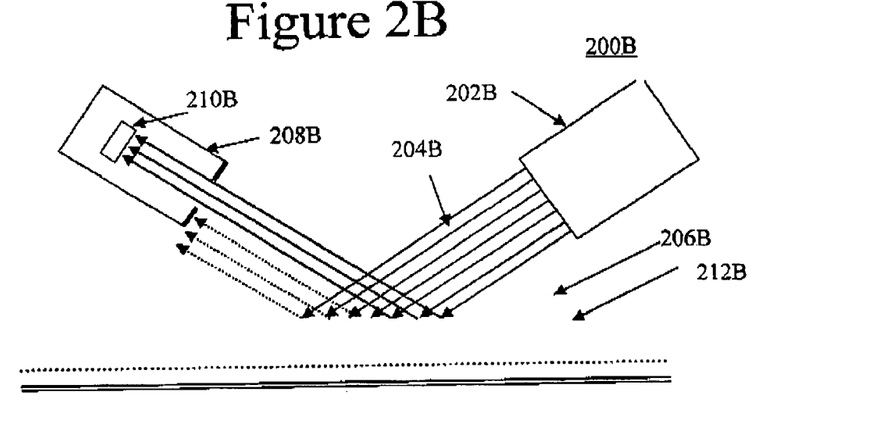
FIG. 2B is a generalized schematic of a sensor used to implement the exemplary light source embodiment of the present invention with flutters and waves of the sample surface at the pass-line.

Referring to FIG. 2B, as the paper moves along the manufacturing process, sample surface 206B of the web of paper may dip, flutter, and wave due to shifts in the web of paper in both lateral and longitudinal directions. The sensor 200B has the light source 202B for providing the light beam 204B to illuminate the sample surface 206B at the pass-line. The light source 202B provides the light beam 204B with an area larger than a light detection surface 210B of the light detector 208B. The sensor 200B provides accurate measurements of the sample surface without or with a reduced need for stabilization. The light beam 204B is reflected off the sample surface 206B. The intensity of the reflected light is measured with the light detector 208B. The reflected light is measured by the light detecting surface 210B of the light detector 208B to determine the light intensity of the reflected beam of light 204B. The shift of the sample surface 206B to a new sample surface angle 212B does not affect the gloss measurement. As long as the light detecting surface 210B remains in the area of the light beam, the intensity detected will remain consistent based on the area of the light detection surface 210B.

Figure 2C:
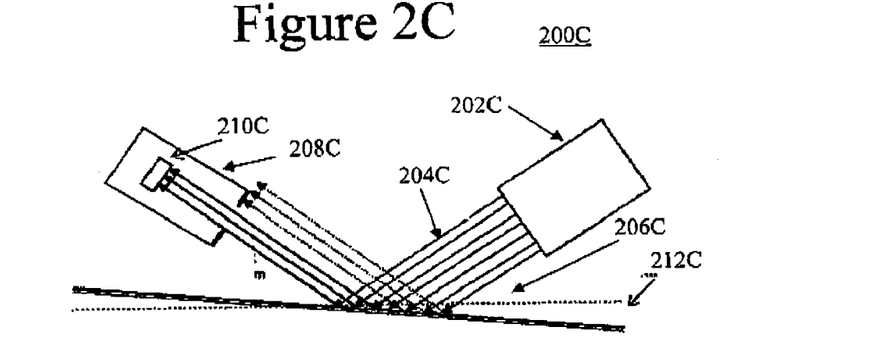
FIG. 2C is a generalized schematic of a sensor used to implement the exemplary light source embodiment of the present invention with a tilted sample surface at the pass-line.

Referring to FIG. 2C, as the paper moves along the manufacturing process, sample surface 206C of the web of paper may tilt and/or cup due to shifts in the web of paper in both lateral and longitudinal directions. The sensor 200C has the light source 202C for providing the light beam 204C to illuminate the sample surface 206C at the pass-line. The light source 202B provides the light beam 204C with an area larger than a light detection surface 210C of the light detector 208C. The sensor 200C provides accurate measurements of the sample surface without or with a reduced need for stabilization. The light beam 204C is reflected off the sample surface 206C. The intensity of the reflected light is measured with the light detector 208C. The reflected light is measured by the light detecting surface 210C of the light detector 208C to determine the light intensity of the reflected beam of light 204C. The tilt of the sample surface 206C to a new sample surface angle 212C does not affect the gloss measurement. As long as the light detecting surface 210C remains in the area of the light beam, the intensity detected will remain consistent based on the area of the light detection surface 210C.

The reference analyzer compares the intensity of the signal received from light detector 210 with known values of intensity for various gloss sample surfaces. Architecturally in terms of hardware, the reference analyzer may include a processor, memory, and one or more input and output interface devices. The local interface may have additional elements, which are omitted for simplicity, such as controllers, buffers (caches), drivers, repeaters, and receivers, to enable communications. Further, the local interface may include address, control, and/or data connections to enable appropriate communications among the components of a network.

The reference analyzer may determine the gloss level of sample surface 206 by determining the ratio of the reflecting light beam intensity to the intensity of the illuminating light beam from the light source 202. The amount of light dispersed by sample surface 206 is used to determine the gloss level of sample surface 206. The reference analyzer may use a stored table or equations to compute the gloss level of the sample surface 206. The gloss level is determined by comparing the ratio of intensity with the intensity of the gloss level for known sample tables of the gloss level.

The systems and methods may also be incorporated in software used with a computer or other suitable operating device of the reference analyzer. The reference analyzer may also include a Graphic User Interface (GUI) to allow the administrator or user to enter, view and store the gloss level or enter constraints associated with the desired gloss level to control other devices of the manufacturing process.

Figure 3:
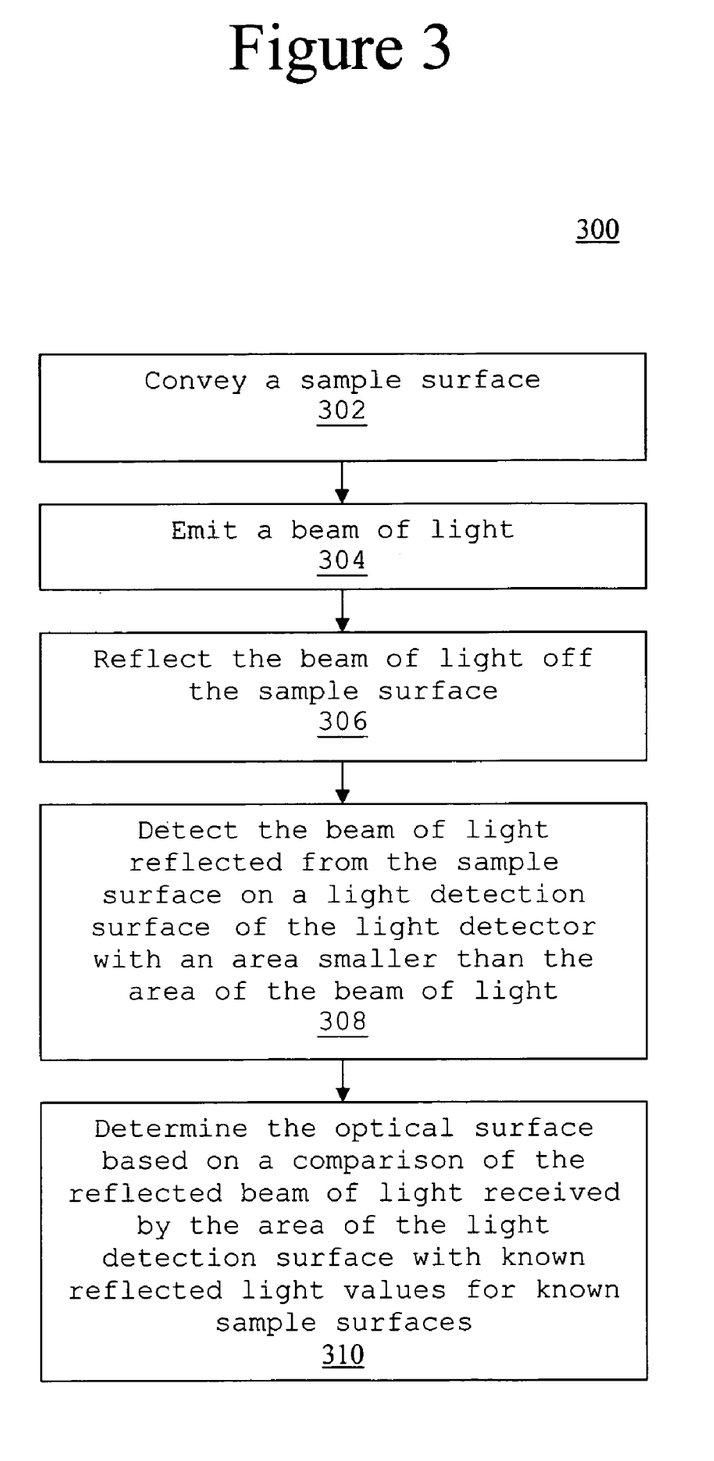
FIG. 3 is a flow chart illustrating an exemplary method for the sensor used to implement the light source embodiment of the present invention.

Referring to FIG. 3, a flow chart illustrates an exemplary method for the sensor used to implement the light source embodiment 300 of the present invention. The manufacturing process advances sample surface 206 to the pass-line of sensor 200 (block 302). The light source 202 directs beam of light 204 onto sample surface 206 (block 304). The beam of light 204 is reflected by sample surface 206 (block 306).

The beam of light reflected by the sample surface is detected on a light detection surface 210 of the light detector 208 (block 308). The light detection surface 210 has an area smaller than the area of the beam of light 204. This allows the sample surface 206 to flutter or tilt within a designated geometry. The designated geometry is controlled by the area of the beam of light 204 relative to the area of detection on the light detecting surface 210. Increasing the area of the light beam 204 may increase the amount of movement allowed by the sample surface 206 to a new location of the sample surface 212. Generally, the area of the beam of light 204 is circular; however, the invention may utilize a variety of shapes with either the beam of light 204 or the area of the light detection surface 210. For example, the beam of light 204 may be a circle and the light detection surface 208 may be a square with a width larger than the diameter of the beam of light 204. The reference analyzer determines the gloss level of the sample surface 206 by comparing the reflected light received from the area of the light detection surface 210 with known reflected light values for known sample surfaces based on the area of the light detection surface 210 (block 310).

Figure 4A:
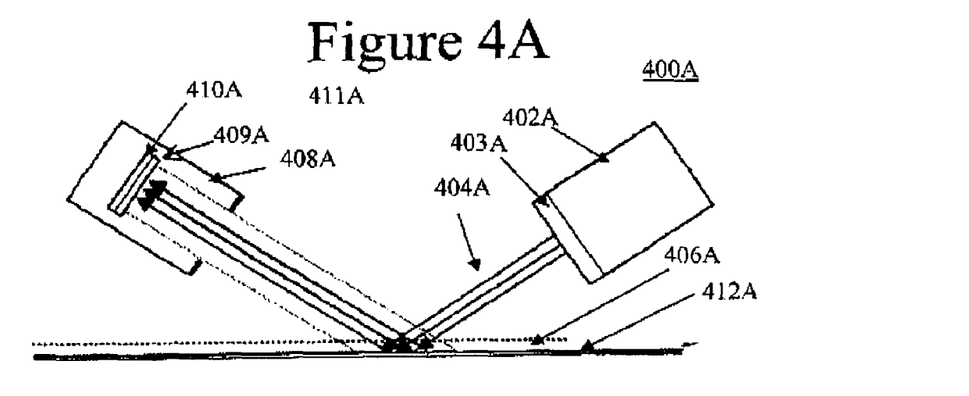
FIG. 4A is a generalized schematic of a sensor used to implement the exemplary light detector embodiment of the present invention.

Referring to FIG. 4A, the sensor 400A may have a light source 402A with lens 403A for providing a light beam 404A to illuminate the sample surface 406A at a pass-line. The light source 402A and lens 403A provide a light beam 404A with an area smaller than a light detection surface 410A of the light detector 408A. The light source 402A provides a focused beam of light 404A as previously described with regard to the exemplary light detector embodiment. The sample surface 406A may also be a variety of materials as previously described with regard to the exemplary light source embodiment.

Sensor 400A provides accurate measurements of sample surface 406A without or with a reduced need for stabilization. Light beam 404A is reflected off sample surface 406A. The intensity of the reflected light is measured with light detector 408A. The reflected light is measured by light detecting surface 410 of light detector 408A to determine the light intensity of the reflected beam of light 404A. The light detecting surface 410A may define the area seen by light detector 408.

Light detecting surface 410A converts the beam of light 404A into electrical current using a variety of light detecting elements as previously described with regard to the exemplary light source embodiment. The signal of light detector 408A is fed into a reference analyzer (not shown). The reference analyzer compares the intensity of the signal received from light detector 410A with known values of intensity for various gloss sample surfaces. Architecturally in terms of hardware, the reference analyzer is similar to the reference analyzer of the exemplary light source embodiment as previously described.

Figure 4B:
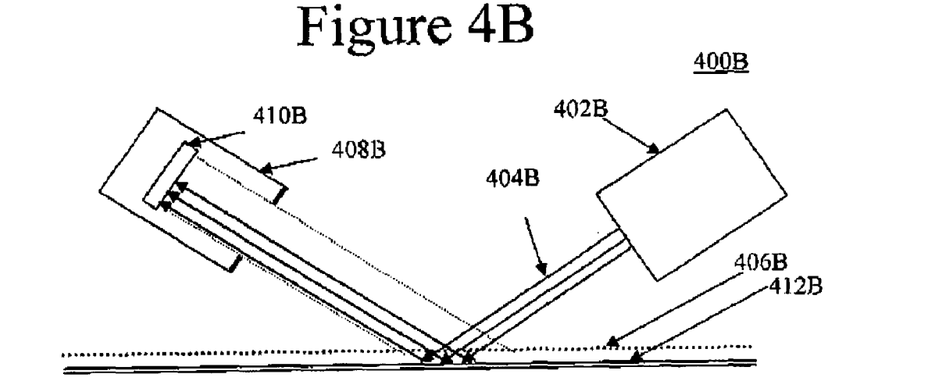
FIG. 4B is a generalized schematic of a sensor used to implement the exemplary light source embodiment of the present invention with flutters and waves of the sample surface at the pass-line.

Referring to FIG. 4B, as the paper moves along the manufacturing process, sample surface 406B of the web of paper may shift, flutter, and wave due to shifts in the web of paper in both lateral and longitudinal directions. Sensor 400B has light source 402B for providing light beam 404B to illuminate sample surface 406B at the pass-line. Light source 402B provides light beam 404B with an area smaller than a light detection surface 410B of light detector 408B. Sensor 400B provides accurate measurements of the sample surface without or with a reduced need for stabilization. Light beam 404B is reflected off sample surface 406B. The intensity of the reflected light is measured with light detector 408B. The reflected light is measured by light detecting surface 410B of light detector 408B to determine the light intensity of the reflected beam of light 404B. The shift of sample surface 406B to a new sample surface angle 412B does not affect the gloss measurement. As long as the beam of light 404B remains in the area of light detecting surface 410B, the intensity detected will remain consistent based on the area of the beam of light 404B.

Figure 4C:
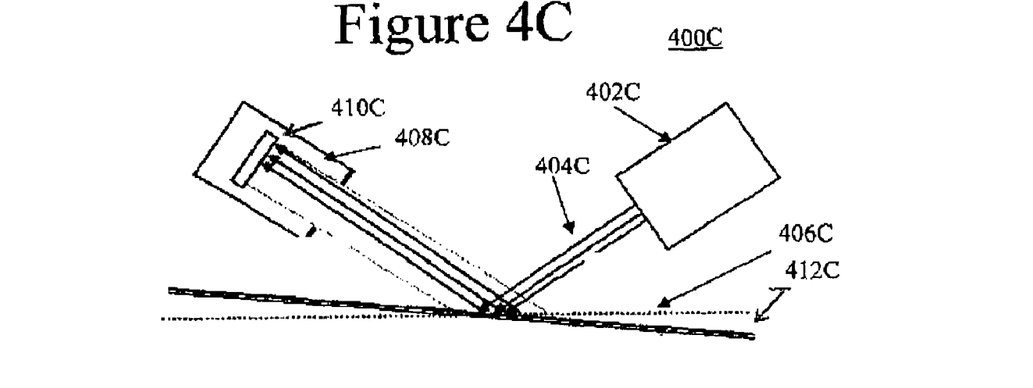
FIG. 4C is a generalized schematic of a sensor used to implement the exemplary light detector embodiment of the present invention with a tilted sample surface at the pass-line.

Referring to FIG. 4C, as the paper moves along the manufacturing process, sample surface 406C of the web of paper may tilt and/or cup due to shifts in the web of paper in both lateral and longitudinal directions. Sensor 400C has light source 402C for providing light beam 404C to illuminate sample surface 406C at the pass-line. Light source 402C provides light beam 404C with an area smaller than a light detection surface 410C of light detector 408C. Sensor 400C provides accurate measurements of the sample surface without or with a reduced need for stabilization. Light beam 404C is reflected off sample surface 406C. The intensity of the reflected light is measured with light detector 408C. The reflected light is measured by light detecting surface 410C of light detector 408C to determine the light intensity of the reflected beam of light 404C. The tilt of sample surface 406C to a new sample surface angle 412C does not affect the gloss measurement. As long as the beam of light 404C remains in the area of light detecting surface 410C, the intensity detected will remain consistent based on the area of the beam of light 404C.

The reference analyzer may determine the gloss level of the sample surface 406 by determining the ratio of the reflecting light beam intensity to the intensity of the illuminating light beam from light source 408. The amount of light dispersed by sample surface 406 is used to determine the gloss level of sample surface 406. The reference analyzer may use a stored table or equations to compute the gloss level of sample surface 406. The gloss level is determined by comparing the ratio of intensity with the intensity of gloss levels for known sample tables of the gloss level.

Figure 5:
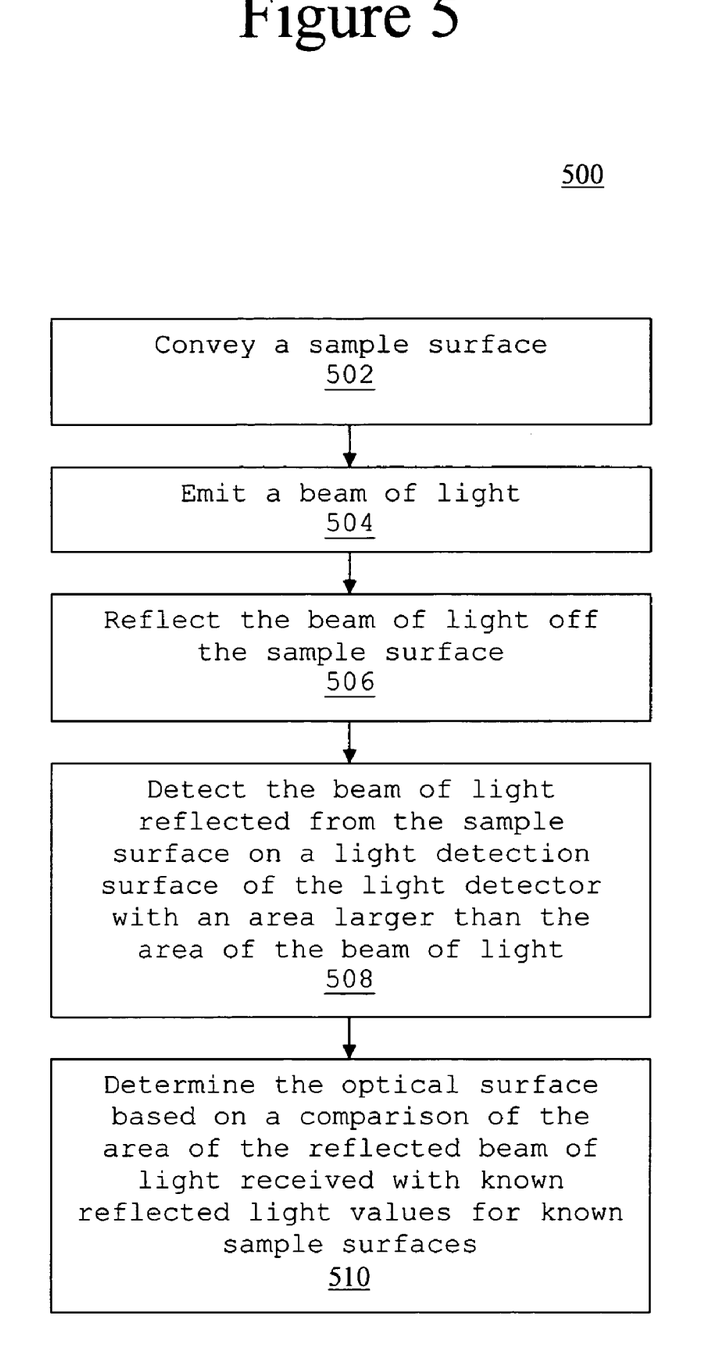
FIG. 5 is a flow chart illustrating an exemplary method for the sensor used to implement the light detector embodiment of the present invention.

Referring to FIG. 5, a flow chart illustrates an exemplary method for the sensor used to implement the light detector embodiment 400 of the present invention. The manufacturing process advances sample surface 406 to the pass-line of sensor 400 (block 502). Light source 402 directs beam of light 404 onto sample surface 406 (block 504). Beam of light 404 is reflected by sample surface 406 (block 506).

Beam of light 404 reflected by the sample surface 406 is detected on light detection surface 410 of light detector 408 (block 508). Light detection surface 410 has an area larger than the area of the beam of light 404. This allows sample surface 406 to flutter or tilt within a designated geometry. The designated geometry is controlled by the area of the beam of light 404 relative to the area of detection on light detecting surface 410. Increasing the area of light beam 404 may increase the amount of movement allowed by sample surface 406 to a new location of sample surface 412. The reference analyzer determines the gloss level of sample surface 406 by comparing the reflected light received from light detection surface 410 with known reflected light values for known sample surfaces based on the area of the beam of light 404 (block 510).

It will be understood that the foregoing is only illustrative of the principles of the invention and that various modifications can be made by those skilled in the art without departing from the scope and spirit of the invention. Accordingly, such embodiments will be recognized as within the scope of the present invention. For example, the exemplary embodiments are illustrated as being implemented to determine the gloss level of the sample surface, however, one skilled in the art will appreciate that embodiments of the invention may be implemented with a variety of other surface characteristics.

Persons skilled in the art will also appreciate that the present invention can be practiced by other than the described embodiments, which are presented for purposes of illustration rather than of limitation and that the present invention is limited only by the claims that follow.

What is claimed is:

1. A device for detecting one or more surface characteristics of a sample surface comprising:
   a light source for reflecting a beam of light off the sample surface;
   a light detector with a light detection surface;
   a lens for receiving the beam of light reflected from the sample surface and focusing the beam of light onto the light detection surface of the light detector, wherein an area of the focused beam of light at a point of focus on the light detection surface is larger than an area of the light detection surface, and wherein the focused beam of light covers the entire area of the light detection surface when the sample surface does and does not move or tilt; and
   an analyzer for determining the one or more surface characteristics of the sample surface based on a comparison of a measurement of the focused beam of light with known reflected light values for known sample surfaces.

2. The device of claim 1, wherein:
   the analyzer comparison is based on the area of the light detection surface.

3. The device of claim 1, wherein the analyzer determines at least one of: a gloss, a deviation of gloss, a sparkle spot size, and a number of spot sizes of the sample surface.

4. The device of claim 1, wherein the light detector comprises at least one of: a Charge Coupled Device (CCD) camera, a CCD array, a Complementary Metal Oxide Semiconductor (CMOS) camera, a CMOS array, and a Photodiode array.

5. The device of claim 1, wherein the sample surface is a surface of a moving web of paper.

6. The device of claim 1, wherein the analyzer compares an intensity of the focused beam of light with known intensity values of the known sample surfaces.

7. The device of claim 1, wherein the focused beam of light moves but continues to cover the entire area of the light detection surface when the sample surface moves or tilts, the movement or tilting occurring within a geometric limit.

8. A method for detecting one or more surface characteristics of a sample surface comprising the acts of:
   emitting a beam of light;
   reflecting the beam of light off the sample surface;
   focusing the beam of light reflected from the sample surface onto a light detection surface of a light detector, wherein an area of the focused beam of light at a point of focus on the light detection surface is larger than an area of the light detection surface, and wherein the focused beam of light covers the entire area of the light detection surface when the sample surface does and does not move or tilt; and
   determining the one or more surface characteristics of the sample surface based on a comparison of a measurement of the focused beam of light with known reflected light values for known sample surfaces.

9. The method of claim 8, wherein the comparison is based on the area of the light detection surface.

10. The method of claim 8, wherein determining the one or more surface characteristics of the sample surface comprises determining at least one of: a gloss, a deviation of gloss, a sparkle spot size, and a number of spot sizes of the sample surface.

11. The method of claim 8, wherein the light detector comprises at least one of: a Charge Coupled Device (CCD) camera, a CCD array, a Complementary Metal Oxide Semiconductor (CMOS) camera, a CMOS array, and a Photodiode array.

12. The method of claim 8, wherein the sample surface is a surface of a moving web of paper.

13. The method of claim 8, wherein determining the one or more surface characteristics of the sample surface comprises comparing an intensity of the focused beam of light with known intensity values of the known sample surfaces.

14. The method of claim 8, wherein the focused beam of light moves but continues to cover the entire area of the light detection surface when the sample surface moves or tilts, the movement or tilting occurring within a geometric limit.

15. A device for detecting one or more surface characteristics of a sample surface comprising:
   a light detector with a light detection surface;
   optics for receiving a beam of light reflected from the sample surface and focusing the beam of light on the light detection surface of the light detector, wherein an area of the focused beam of light at a point of focus on the light detection surface is larger than an area of the light detection surface, and wherein the focused beam of light covers the entire area of the light detection surface when the sample surface does and does not move or tilt; and
   an analyzer for determining the one or more surface characteristics of the sample surface based on a comparison of a measurement of the focused beam of light with known reflected light values for known sample surfaces.

16. The device of claim 15, wherein the analyzer performs the comparison based on the area of the light detection surface.

17. The device of claim 15, wherein the analyzer determines at least one of: a gloss, a deviation of gloss, a sparkle spot size, and a number of spot sizes of the sample surface.

18. The device of claim 15, wherein the sample surface is a surface of a moving web of paper.

19. The device of claim 15, wherein the analyzer compares an intensity of the focused beam of light with known intensity values of the known sample surfaces.

20. The device of claim 15, wherein the focused beam of light moves but continues to cover the entire area of the light detection surface when the sample surface moves or tilts, the movement or tilting occurring within a geometric limit.

* * * * *